(12) United States Patent  
Gyory

(10) Patent No.: US 11,174,852 B2  
(45) Date of Patent: Nov. 16, 2021

(54) RECIPROCATING PUMP

(71) Applicant: Becton, Dickinson and Company, Franklin Lakes, NJ (US)

(72) Inventor: J. Richard Gyory, Sudbury, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 421 days.

(21) Appl. No.: 16/041,068

(22) Filed: Jul. 20, 2018

(65) Prior Publication Data

US 2020/0025184 A1 Jan. 23, 2020

(51) Int. Cl.
| | |
|---|---|
| F04B 7/00 | (2006.01) |
| F04B 49/06 | (2006.01) |
| A61M 5/145 | (2006.01) |
| A61M 5/168 | (2006.01) |
| A61M 5/142 | (2006.01) |

(52) U.S. Cl.
CPC ......... F04B 7/0061 (2013.01); A61M 5/1452 (2013.01); A61M 5/14248 (2013.01); A61M 5/14586 (2013.01); A61M 5/16881 (2013.01); F04B 49/06 (2013.01)

(58) Field of Classification Search
CPC .... F04B 7/0057; F04B 7/0061; F04B 7/0069; F04B 9/04; F04B 9/042; F04B 9/047; F04B 9/06; F04B 49/06; F04B 53/1072; F04B 53/1075; A61M 5/1452; A61M 5/14586; A61M 5/16881; A61M 39/28; A61M 5/14248
See application file for complete search history.

(56) References Cited

U.S. PATENT DOCUMENTS

| | | | | |
|---|---|---|---|---|
| 1,866,217 | A | * 7/1932 | Mayer | F04B 7/06 417/500 |
| 3,914,073 | A | * 10/1975 | Fusco | B41F 31/08 417/500 |
| 4,067,668 | A | * 1/1978 | Nimell | F04B 7/06 417/492 |
| 5,385,992 | A | 1/1995 | Koskinen et al. | |
| 5,913,180 | A | 6/1999 | Ryan | |
| 6,435,844 | B1 | 8/2002 | Fukami | |

(Continued)

FOREIGN PATENT DOCUMENTS

| | | |
|---|---|---|
| DE | 4209690 A1 | 9/1993 |
| DE | 102009026740 A1 | 12/2010 |

(Continued)

OTHER PUBLICATIONS

EP-0042900-A1 English Translation, (Year: 1982).*

*Primary Examiner* — Dominick L Plakkoottam  
*Assistant Examiner* — Charles W Nichols  
(74) *Attorney, Agent, or Firm* — Dickinson Wright PLLC

(57) ABSTRACT

A pump suitable for use in a wearable medical device, such as a patch pump, comprises an axially translatable chamber with an inlet and an outlet, a piston or a diaphragm rotatably received in the chamber, a first valve between the inlet and the chamber, a second valve between the outlet and the chamber, a cam affixed to the chamber, a follower affixed to the piston and in contact with the cam for axially translating the chamber, and a biasing means acting on the chamber for applying a force on the chamber in an axial direction of the chamber to maintain such contact.

18 Claims, 5 Drawing Sheets

(56) References Cited

U.S. PATENT DOCUMENTS

| | | | |
|---|---|---|---|
| 6,461,331 B1 | 10/2002 | Antwerp | |
| 6,740,059 B2 | 5/2004 | Flaherty | |
| 7,029,249 B2 | 4/2006 | Bougamont et al. | |
| 7,052,251 B2 | 5/2006 | Nason et al. | |
| 7,104,275 B2 * | 9/2006 | Dille | F16K 7/045 137/487.5 |
| 7,303,549 B2 | 12/2007 | Flaherty et al. | |
| 7,517,440 B2 | 4/2009 | Anex et al. | |
| 7,726,955 B2 | 6/2010 | Ryser et al. | |
| 7,887,308 B2 | 2/2011 | Navarro | |
| 7,976,505 B2 | 7/2011 | Hines et al. | |
| 8,114,064 B2 | 2/2012 | Alferness et al. | |
| 8,162,923 B2 | 4/2012 | Adams et al. | |
| 8,187,228 B2 | 5/2012 | Bikovsky | |
| 8,202,250 B2 | 6/2012 | Stutz, Jr. | |
| 8,226,607 B2 | 7/2012 | Carter et al. | |
| 8,282,366 B2 | 10/2012 | Hilber et al. | |
| 8,287,495 B2 | 10/2012 | Michaud et al. | |
| 8,298,184 B2 | 10/2012 | DiPerna et al. | |
| 8,353,688 B2 | 1/2013 | Navarro | |
| 8,448,824 B2 | 5/2013 | DiPerna | |
| 8,469,930 B2 | 6/2013 | Haueter et al. | |
| 8,500,700 B2 | 8/2013 | Haueter et al. | |
| 8,641,671 B2 | 2/2014 | Michaud et al. | |
| 8,957,674 B2 | 2/2015 | Genoud et al. | |
| 9,022,755 B2 | 5/2015 | Junod et al. | |
| 9,095,650 B2 | 8/2015 | Matsuura et al. | |
| 9,119,911 B2 | 9/2015 | Haueter et al. | |
| 9,222,470 B2 | 12/2015 | Genoud et al. | |
| 9,421,327 B2 | 8/2016 | Niklaus et al. | |
| 9,427,517 B2 | 8/2016 | Eberhard | |
| 9,446,193 B2 | 9/2016 | Geipel et al. | |
| 9,662,453 B2 | 5/2017 | Teutsch et al. | |
| 9,726,172 B2 | 8/2017 | Wattellier et al. | |
| 9,889,253 B2 | 2/2018 | Niklaus et al. | |
| 9,970,436 B2 | 5/2018 | Navarro et al. | |
| 10,034,977 B2 | 7/2018 | Haueter et al. | |
| 11,009,018 B2 * | 5/2021 | Wyss | F04B 19/22 |
| 2004/0026461 A1 | 2/2004 | Bougamont et al. | |
| 2009/0112155 A1 | 4/2009 | Zhao et al. | |
| 2009/0123309 A1 | 5/2009 | Hilber et al. | |
| 2009/0292245 A1 | 11/2009 | Basso et al. | |
| 2010/0057006 A1 | 3/2010 | Cassemeyer et al. | |
| 2010/0065579 A1 | 3/2010 | DiPerna | |
| 2010/0185175 A1 | 7/2010 | Kamen et al. | |
| 2011/0060280 A1 | 3/2011 | Caffey et al. | |
| 2011/0137255 A1 | 6/2011 | Nielsen et al. | |
| 2011/0144586 A1 | 6/2011 | Michaud et al. | |
| 2011/0152824 A1 | 6/2011 | DiPerna et al. | |
| 2012/0126795 A1 | 5/2012 | Genoud et al. | |
| 2012/0215200 A1 | 8/2012 | Matsuura et al. | |
| 2013/0017099 A1 | 1/2013 | Genoud et al. | |
| 2013/0053816 A1 | 2/2013 | DiPerna et al. | |
| 2013/0089437 A1 | 4/2013 | Kennedy | |
| 2013/0317324 A1 | 11/2013 | Yodfat et al. | |
| 2013/0324928 A1 | 12/2013 | Kruse | |
| 2015/0297825 A1 | 10/2015 | Focht et al. | |
| 2016/0160854 A1 | 6/2016 | Dehan et al. | |
| 2016/0195074 A1 | 7/2016 | Beard et al. | |
| 2016/0195075 A1 | 7/2016 | Adams | |
| 2016/0213851 A1 | 7/2016 | Weibel et al. | |
| 2017/0184091 A1 | 6/2017 | Focht et al. | |
| 2019/0321556 A1 | 10/2019 | McKinnon | |

FOREIGN PATENT DOCUMENTS

| | | | | |
|---|---|---|---|---|
| EP | 0042900 A1 * | 1/1982 | | F23K 5/145 |
| JP | S5390005 A | 8/1978 | | |
| JP | S58113586 A | 7/1983 | | |
| JP | S60252173 A | 12/1985 | | |
| JP | H03260377 A | 11/1991 | | |
| JP | 2001132621 A | 5/2001 | | |
| JP | 2002202066 A | 7/2002 | | |
| JP | 2004263656 A | 9/2004 | | |
| WO | 2013005159 A1 | 1/2013 | | |
| WO | 2013046156 A1 | 4/2013 | | |
| WO | 2015157174 A1 | 10/2015 | | |

* cited by examiner

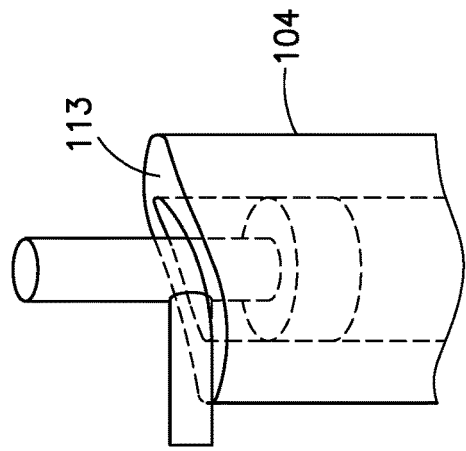
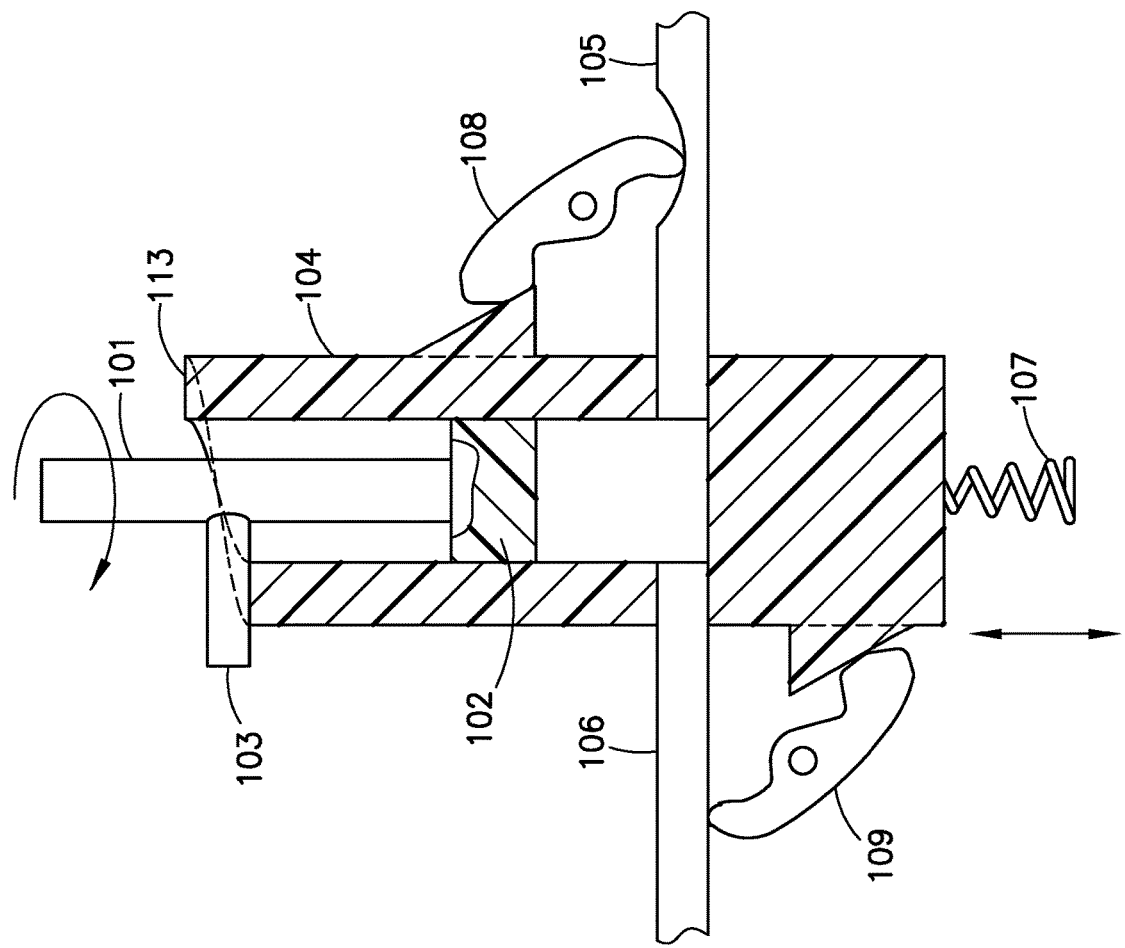

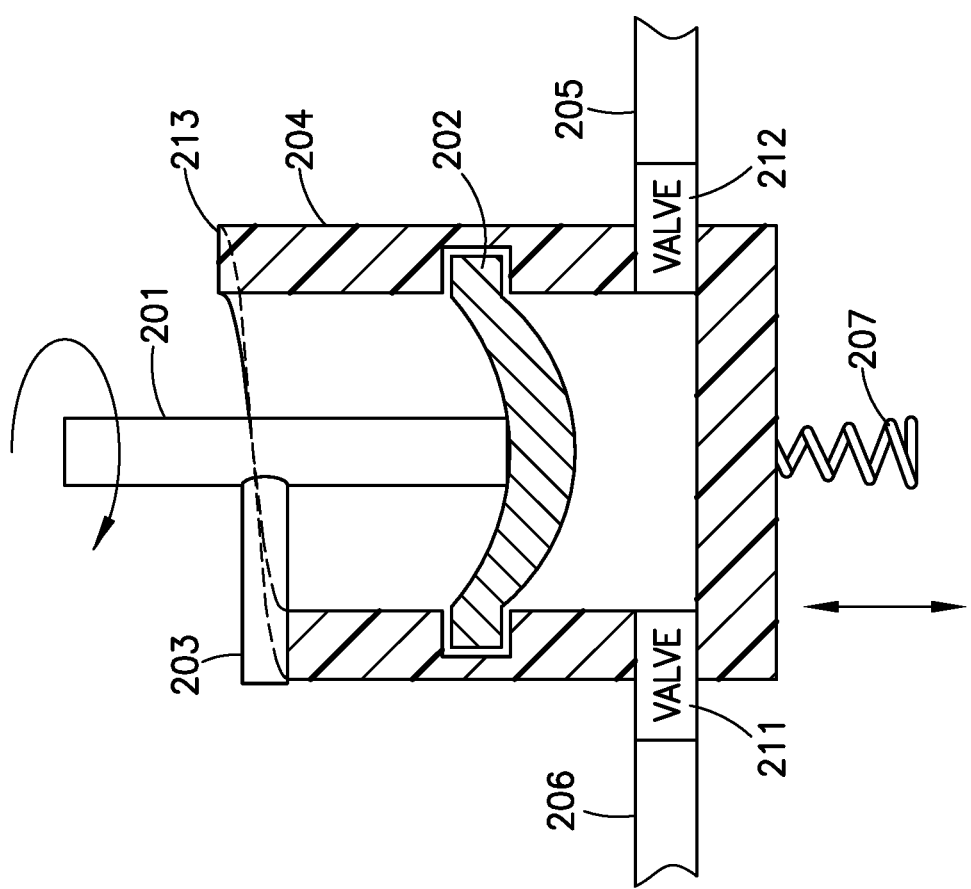

RECIPROCATING PUMP

FIELD OF THE INVENTION

The present invention relates generally to a compact, precise, reliable and low cost pump suitable for subcutaneous delivery of a liquid pharmaceutical product. More particularly, embodiments of the present invention relate to a pump with a piston or diaphragm that undergoes a rotational motion. The pharmaceutical product to be delivered may be insulin for diabetic patients.

BACKGROUND OF THE INVENTION

Diabetes is a group of diseases marked by high levels of blood glucose resulting from defects in insulin production, insulin action, or both. There are 23.6 million people in the United States, or 8% of the population, who have diabetes. The total prevalence of diabetes has increased 13.5% since the 2005-2007 time period. Diabetes can lead to serious complications and premature death, but there are well-known products available for people with diabetes to help control the disease and lower the risk of complications.

Treatment options for people with diabetes include specialized diets, oral medications and/or insulin therapy. The primary goal for diabetes treatment is to control the patient's blood glucose (sugar) level in order to increase the chances of a complication-free life. It is not always easy, however, to achieve good diabetes management, while balancing other life demands and circumstances.

Currently, there are two principal modes of daily insulin therapy for the treatment of type 1 diabetes. The first mode includes syringes and insulin pens that require a needle stick at each injection, typically three to four times per day that are simple to use and relatively low in cost. Another widely adopted and effective method of treatment for managing diabetes is the use of an insulin pump. Insulin pumps can help the user keep blood glucose levels within target ranges based on individual needs, by continuous infusion of insulin. By using an insulin pump, the user can match insulin therapy to lifestyle, rather than matching lifestyle to how an insulin injection is working for the user.

Conventional insulin pumps are capable of delivering rapid or short-acting insulin 24 hours a day through a catheter placed under the skin. Insulin doses are typically administered at a basal rate and in a bolus dose. Basal insulin is delivered continuously over 24 hours, and keeps the user's blood glucose levels in a consistent range between meals and overnight. Some insulin pumps are capable of programming the basal rate of insulin to vary according to the different times of the day and night. Bolus doses are typically administered when the user takes a meal, and generally provide a single additional insulin injection to balance the carbohydrates consumed. Some conventional insulin pumps enable the user to program the volume of the bolus dose in accordance with the size or type of the meal consumed. Conventional insulin pumps also enable a user to take in a correctional or supplemental bolus of insulin to compensate for a low blood glucose level at the time the user is calculating a meal bolus.

There are many advantages of conventional insulin pumps over other methods of diabetes treatment. Insulin pumps deliver insulin over time rather than in single injections and thus typically result in less variation within the blood glucose range that is recommended by the American Diabetes Association. Conventional insulin pumps also reduce the number of needle sticks which the patient must endure, and make diabetes management easier and more effective for the user, thus considerably enhancing the quality of the user's life.

A major disadvantage of existing insulin pumps is that, in spite of their portability, they include multiple components and can be heavy and cumbersome to use. They are also typically more expensive than other methods of treatment. From a lifestyle standpoint, the conventional pump with its associated tubing and infusion set can be inconvenient and bothersome for the user.

Unlike a conventional infusion pump, a patch pump is an integrated device that combines most or all of the fluidic components, including the fluid reservoir, pumping mechanism and a mechanism for automatically inserting the cannula, in a single housing which is adhesively attached to an infusion site on the patient's skin, and does not require the use of a separate infusion or tubing set. Some patch pumps wirelessly communicate with a separate controller (as in one device sold by Insulet Corporation under the brand name OmniPod®), while others are completely self-contained. Such devices are replaced on a frequent basis, such as every three days, when the insulin supply is exhausted.

As a patch pump is designed to be a self-contained unit that is worn by the diabetic patient, it is preferable to be as small as possible so that it does not interfere with the activities of the user. In order to minimize discomfort to the user, it is preferable to minimize the overall dimension of the patch pump. However, in order to minimize the overall dimensions of the patch pump, its constituent parts should be reduced in size as much as possible.

Accordingly, there is a need in the art for a liquid pump that is precise, compact and cost-effective, so that it can be provided as part of a disposable system such as a patch pump.

It is an object of exemplary embodiment of the present invention to provide a precise, compact, cost-effective pump for a wearable medical device, so that more diabetes patients can benefit from the advantages these devices provide.

SUMMARY OF THE INVENTION

According to one embodiment of the present invention, there is provided a pump for the pumping of a liquid, said pump comprising an axially translatable chamber with an inlet and an outlet, a piston or a diaphragm rotatably received in the chamber, a first valve between the inlet and the chamber, a second valve between the outlet and the chamber, a cam affixed to the chamber, a follower affixed to the piston and in contact with the cam for axially translating the chamber, and a biasing means acting on the chamber for applying a force on the chamber in an axial direction of the chamber to maintain such contact.

An advantage of a pump according to an embodiment of the present invention is that very small and precise amounts of liquid medicament can be pumped per revolution of the piston or a diaphragm. This enables small liquid dosages to be injected very precisely, and as a result, higher drug concentration in the reservoir becomes possible. Higher drug concentration further reduces the size of the drug reservoir and prolongs the replacement interval between reservoir cartridges. Due to the compact size of a pump according to an embodiment of the present invention, it may be employed in a wearable patch pump or otherwise positioned close to the point of injection.

According to another aspect of the present invention, there is provided a method for operating a pump comprising an axially translatable chamber with an inlet and an outlet, a piston or diaphragm rotatably received in the chamber, a first valve between the inlet and the chamber, and a second valve between the outlet and the chamber, the method comprising the steps of rotating the piston or diaphragm, translating the rotation of the piston or diaphragm into axial reciprocation of the chamber and opening and closing the first and second valves to allow liquid to be drawn into and expelled from the chamber by the piston or diaphragm.

BRIEF DESCRIPTION OF THE DRAWINGS

The above and other exemplary objects, features and advantages of the present invention will become more apparent from the following description of certain exemplary embodiments thereof when taken in conjunction with the accompanying drawings, in which:

FIGS. 2A and 2B are cross-sectional and partial upper perspective views, respectively, of a pump system according to a second embodiment of present invention;

FIGS. 3A and 3B are cross-sectional views of a pump system according to a third embodiment of the present invention, shown during different portions of the pumping cycle;

Throughout the drawings, like reference numerals will be understood to refer to like elements, features and structures.

DETAILED DESCRIPTION OF EXEMPLARY EMBODIMENTS

The matters exemplified in this description are provided to assist in an understanding of exemplary embodiments of the invention, and are made with reference to the accompanying drawings. Descriptions of well-known functions and constructions are omitted for clarity and conciseness.

Figure 1B:
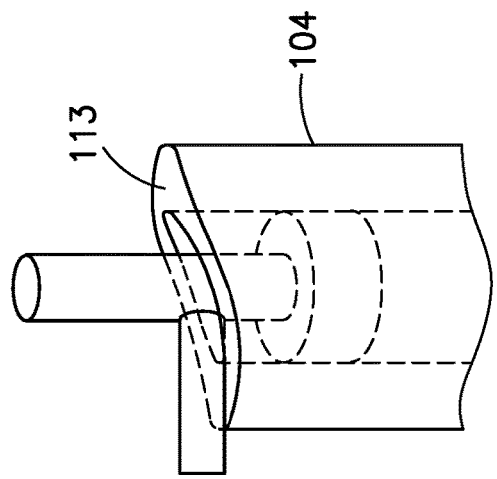
FIGS. 1A and 1B are cross-sectional and partial upper perspective views, respectively, of a pump system according to a first embodiment of the present invention.
Figure 1A:
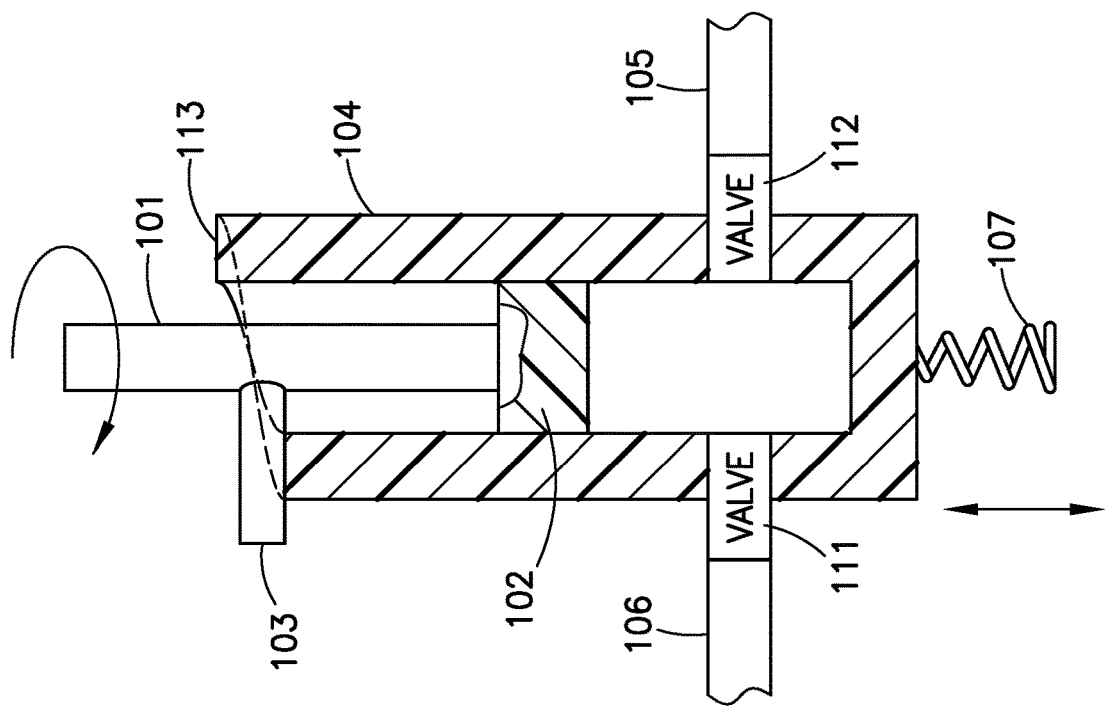

As shown in FIGS. 1A and 1B, a pump according to a first embodiment of the present invention is illustrated in cross-sectional and partial upper perspective views. The pump comprises a chamber 104 within which a piston 102 is rotatably received. A shaft or piston rod 101 is rigidly connected to the piston 102. A post 103 is rigidly connected to the shaft 101 and serves as a cam follower for contacting a cam surface 113 that extends around the top edge of the chamber 104. In this embodiment, the piston 102 only rotates inside the chamber 104 and does not engage in any movement in the axial direction of the chamber 104. Instead, it is the chamber 104 that reciprocates axially as the rotation of the shaft 101 is translated to axial motion of the chamber 104 by virtue of the cam surface 113 and the post 103. This design is mechanically less complicated than conventional designs because it does not require a rotating linkage that is capable of axial sliding. This design also increases reliability and reduces cost of manufacturing. The benefits of this design similarly apply to the embodiments of FIGS. 2A-2B and 3A-3C below.

The chamber 104 comprises an inlet 105, an outlet 106, an inlet valve 112 and an outlet valve 111. The valves 111 and 112 may be self-activating check valves, or externally controlled valves that are operated in sequence by a suitable mechanical linkage or electrical control system (not shown). A biasing means 107 such as a coil spring acts on the chamber 104 for applying an upward biasing force on the bottom of the chamber 104 in an axial direction of the chamber 104. The biasing means 107 maintains constant contact between the post 103 and the cam surface 113, causing the chamber 104 to translate up and down along the axial direction of the chamber 104. The rotational motion of the post 103 and the piston 102 is transformed into linear motion of the chamber 104. When the post 103 rotates, it pushes the cam surface 113 of the chamber 104.

The opening and closing of valves 111 and 112 is synchronized with the rotation of the post 103. Both the inlet valve 112 and the outlet valve 111 open and close as a function of the relative displacement between the post 103 and the cam surface 113 to allow liquid to flow in and out of the chamber 104.

The biasing means 107 maintains an appropriate pressure to maintain constant contact between the post 103 and the cam surface 113 throughout the pumping cycle. The pumping process repeats itself to maintain a steady flow of fluid through the chamber 104.

FIGS. 2A and 2B are cross-sectional and partial upper perspective views of a pump according to another embodiment of present invention. Similar to FIGS. 1A and 1B, a biasing means 107 acts on the chamber 104 for applying a force on the chamber 104 in an axial direction of the chamber 104 to maintain constant contact between the post 103 and the cam surface 113. The interaction between the post 103 and the cam surface 113 causes the chamber 104 to translate up and down along the axial direction of the chamber 104.

When the post 103 rotates to a certain position, the cam surface 113 and the chamber 104 are pushed downward by the post 103, and the pinch valve 109 is triggered to close the flexible outlet conduit 106. When post rotates to another position, the chamber 104 is pushed upward by the biasing means 107, the pinch valve 108 is triggered to close the flexible inlet conduit 105. The pumping process repeats itself to maintain a steady flow of fluid through the chamber 104.

Figure 3C:
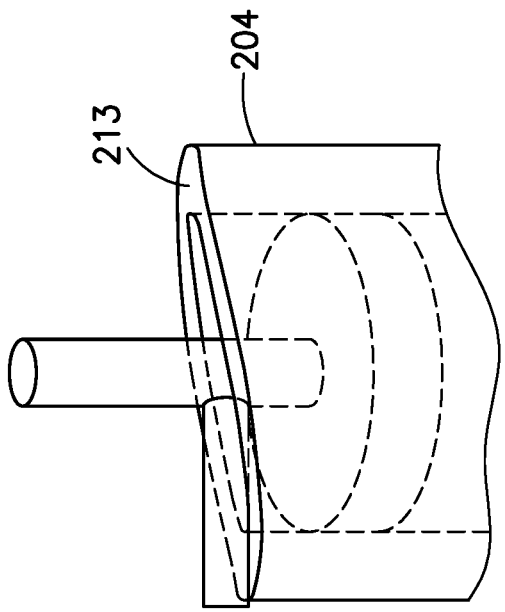
FIG. 3C is a partial upper perspective view of the pump system of FIGS. 3A and 3B.
Figure 3B:
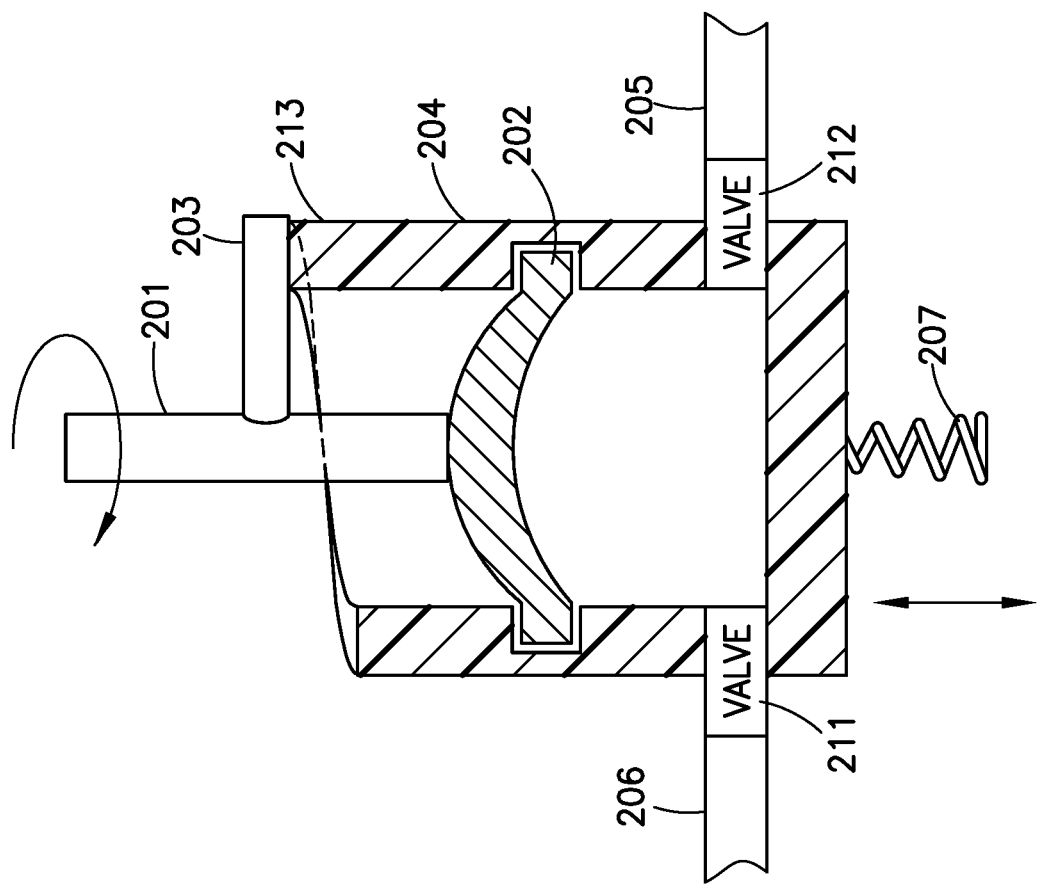

In FIGS. 3A-3C, a pump according to a third embodiment of the present invention is illustrated in cross-sectional and partial upper perspective views. The pump comprises a chamber 204 within which a flexible diaphragm 202 is rotatably received. A shaft 201 is rigidly connected to the diaphragm 202. A post 203 is rigidly connected to the shaft 201. Analogous to the previous embodiment, the diaphragm 202 only rotates inside the chamber 204 and does not engage in movement in the axial direction. The chamber 204 comprises an inlet 205, an outlet 206, an inlet valve 212 and an outlet valve 211. A biasing means 207 such as a coil spring acts on the chamber 204 for applying a biasing force on the chamber 204 in an axial direction of the chamber 204. The biasing means 207 maintains constant contact between the post 203 and the cam surface 213. The axial translation of the chamber 204 is coordinated with the opening and closing of the inlet valve 212 and outlet valve 211. The valves 211 and 212 may be self-activating check valves, or externally controlled valves that are operated in sequence by a suitable mechanical linkage or electrical control system (not shown). The opening and closing of the inlet valve 212 and the outlet valve 211 can be mechanically synchronized with the displacement of the post 203 and the cam surface 213.

The outlet valve 211 is opened to allow fluid to be pumped out of the chamber 204 when the cam surface 213 is pushed upward by the biasing means 207. The diaphragm is in the flexed-down position as illustrated in FIG. 3A. The inlet valve 212 is opened to allow fluid to be pumped into the chamber 204 when the cam surface 213 is pushed downward by the post 203. The diaphragm 202 is in the flexed-up position as illustrated in FIG. 3B.

Figure 4:
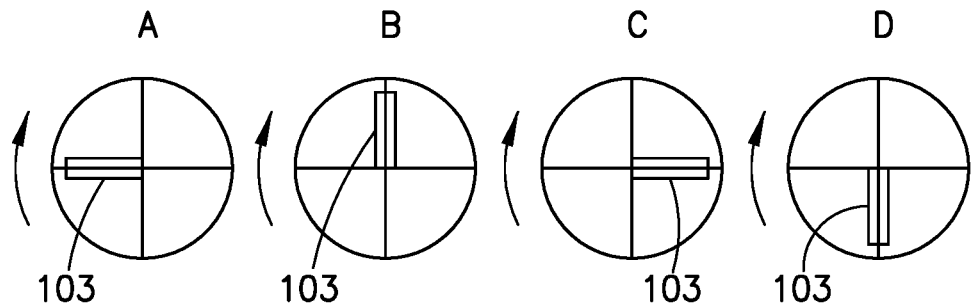
FIG. 4 is an illustration of the states of the inlet and outlet valves with respect to the angular displacement of the rotary piston in the embodiment of FIGS. 1A-1B and 2A-2B.

FIG. 4 is an illustration of the states of the inlet and outlet valves with respect to the angular displacement of the post 103 in the embodiments of FIGS. 1A-1B and 2A-2B. In the first angular displacement A, the inlet valve is open and the outlet valve is closed to allow fluid to flow into the chamber. In the second angular displacement B, both the inlet and the outlet valves are closed. In the third angular displacement C, the inlet valve is closed and the outlet valve is open to allow fluid to flow out of the chamber. In the fourth angular displacement D, both the inlet and the outlet valves are closed. The post 103 then rotates back to the first angular displacement A and a new pumping cycle starts. The pumping cycles are repeated to allow continuous pumping of fluid into and out of the chamber 104 of the pump.

Figure 5:
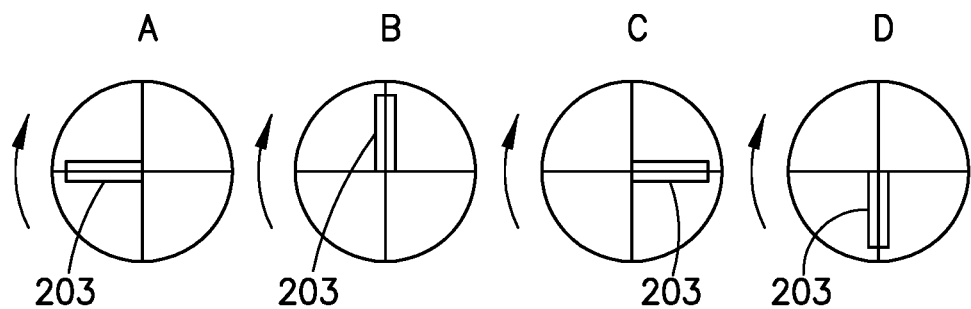
FIG. 5 is an illustration of the states of the inlet and outlet valves and the diaphragm with respect to the angular displacement of the rotary rod in the embodiment of FIGS. 3A-3C.

FIG. 5 is an illustration of the states of the inlet and outlet valves and the diaphragm with respect to the angular displacement of the post 203 in the embodiment of FIGS. 3A-3C. In the first angular displacement A, the diaphragm 202 is flexed down, the inlet valve is closed and the outlet valve is open to allow fluid to flow out of the chamber. In the second angular displacement B, both the inlet and the outlet valves are closed. In the third angular displacement C, the diaphragm 202 is flexed up, the inlet valve is open and the outlet valve is closed to allow fluid to flow into the chamber. In the fourth angular displacement D, both the inlet and the outlet valves are closed. The post 203 then rotates back to the first angular displacement 610 and a new pumping cycle starts. The pumping cycles are repeated to allow continuous pumping of fluid into and out of the chamber 204 of the pump.

While the present invention has been shown and described with reference to particular illustrative embodiments, it is not to be restricted by the exemplary embodiments but only by the appended claims and their equivalents. It is to be appreciated that those skilled in the art can change or modify the exemplary embodiments without departing from the scope of the present invention. In addition, the features of the various embodiments can be combined with each other to form new embodiments without departing from the scope of the present invention.

What is claimed is:

1. A pump system for the pumping of a liquid, the pump system comprising:
    an axially translatable chamber with an inlet and an outlet;
    a piston rotatably received in the chamber;
    a first valve between the inlet and the chamber;
    a second valve between the outlet and the chamber;
    a cam affixed to the chamber;
    a follower affixed to the piston and in contact with the cam for axially translating the chamber; and
    a biasing means acting on the chamber for applying a force on the chamber in an axial direction of the chamber to maintain such contact.

2. The pump system according to claim 1, wherein the first and second valves comprise check valves.

3. The pump system according to claim 1, wherein the first and second valves are operated mechanically.

4. The pump system according to claim 1, wherein the first and second valves are operated electrically.

5. The pump system according to claim 1, wherein the first and second valves comprise pinch valves.

6. The pump system according to claim 1, wherein the biasing means comprises a spring.

7. The pump system according to claim 1, wherein the cam is on an edge of the chamber.

8. A pump system for the pumping of a liquid, the pump system comprising:
    an axially translatable chamber with an inlet and an outlet;
    a diaphragm rotatably received in the chamber;
    a first valve between the inlet and the chamber;
    a second valve between the outlet and the chamber;
    a cam affixed to the chamber;
    a follower affixed to the diaphragm and in contact with the cam for axially translating the chamber; and
    a biasing means acting on the chamber for applying a force on the chamber in an axial direction of the chamber to maintain such contact.

9. The pump system according to claim 8, wherein the first and second valves comprise check valves.

10. The pump system according to claim 8, wherein the first and second valves are operated mechanically.

11. The pump system according to claim 8, wherein the first and second valves are operated electrically.

12. The pump system according to claim 8, wherein the first and second valves comprise pinch valves.

13. The pump system according to claim 8, wherein the biasing means comprises a spring.

14. The pump system according to claim 8, wherein the cam is on an edge of the chamber.

15. A method for operating a pump comprising an axially translatable chamber with an inlet and an outlet, a piston or diaphragm rotatably received in the chamber, a first valve between the inlet and the chamber, and a second valve between the outlet and the chamber, the method comprising:
    rotating the piston or diaphragm;
    translating the rotation of the piston or diaphragm into axial reciprocation of the chamber; and
    opening and closing the first and second valves to allow liquid to be drawn into and expelled from the chamber by the piston or diaphragm.

16. The pump system according to claim 1, wherein the piston only rotates in the chamber and does not move axially.

17. The pump system according to claim 8, wherein the diaphragm only rotates in the chamber and does not move axially.

18. The method according to claim 15, wherein the piston or diaphragm only rotates in the chamber and does not move axially.

* * * * *